(12) United States Patent
Liddell

(10) Patent No.: US 6,180,376 B1
(45) Date of Patent: *Jan. 30, 2001

(54) EXTRACTION OF TRIGLYCERIDES FROM MICROORGANISMS

(75) Inventor: John Macdonald Liddell, Eaglescliffe (GB)

(73) Assignee: Zeneca Limited, London (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/983,250

(22) PCT Filed: Jul. 16, 1996

(86) PCT No.: PCT/GB96/01703

§ 371 Date: Jan. 20, 1998

§ 102(e) Date: Jan. 20, 1998

(87) PCT Pub. No.: WO97/04121

PCT Pub. Date: Feb. 6, 1997

(30) Foreign Application Priority Data

Jul. 18, 1995 (GB) .................................................. 9514649

(51) Int. Cl.[7] ...................................................... C12P 7/64
(52) U.S. Cl. ........................................... 435/134; 435/911
(58) Field of Search ..................................... 435/134, 511

(56) References Cited

U.S. PATENT DOCUMENTS 4,341,038 * 7/1982 Bloch et al. .............................. 47/1.4
4,870,011 * 9/1989 Suzuki et al. .......................... 435/134
5,130,242 * 7/1992 Barclay ................................. 435/134

FOREIGN PATENT DOCUMENTS

| 522 470 | 1/1993 | (EP) . |
| 1 089 093 | 11/1967 | (GB) . |
| 92/13086 | 8/1992 | (WO) . |

OTHER PUBLICATIONS

Shimizu et al. Biochemical and Biophysical Research Communications. Jan. 1988, vol. 150, No. 1, pp. 335–341.*
Talaro et al. In: Foundations in Microbiology. W. C. Brown Publishers, 1993. p. 100.*
Morris et al. Counter–current distribution. In:Separation Methods in biochemistry. Ed.Morris and Morris. Pitman Publishing. 1976. p. 639.*
Database WPI, Section Ch, Week 8413, Derwent publications Ltd., Class D16,AN 84–077725, XP002018398 & JP,A,59 028 480, Feb. 15, 1984.
Patent Abstract of Japan, vol. 008, No. 114 (C–225), May 25, 1984 & JP,A,59 028480, Feb. 15, 1984.

* cited by examiner

Primary Examiner—Irene Marx
Assistant Examiner—Vera Afremova
(74) Attorney, Agent, or Firm—Pillsbury Madison & Sutro LLP

(57) ABSTRACT

Oil is extracted from oil containing microorganisms by disintegrating the microorganisms and contacting them in the presence of a water content of at least 70% by weight of that originally present in the cellular material with a water immiscible solvent for the oil, separating the solvent from the microorganisms and recovering the oil from the solvent.

18 Claims, No Drawings

EXTRACTION OF TRIGLYCERIDES FROM MICROORGANISMS

This application is the national phase of international application PCT/GB96/01703 filed Jul. 16, 1996 which designated the U.S.

This invention relates to an extraction process.

Vegetable oils can be extracted from dried plant seeds using pressure. This in general leaves vegetable oil in the crushed plant tissue and this may be extracted using a water-immiscible organic solvent, for example hexane.

It is possible to extract microbial oils from whole microbes by hexane extraction. The microbial material must be dried usually to a water content of less than 5% (w/w) before the oil can be effectively extracted by hexane. Not only does this involve a considerable consumption of energy because, in general, microbial cells contain at least 70% for example 80 to 95% (w/w) water based on their non-oil content, but we have also found that sensitive oils for example oxygen or heat sensitive oils may undergo chemical reactions in the drying process.

In alternative methods of extracting oils from microorganisms, water-miscible solvents, for example isopropanol, may be used. Such extractions are in general less selective than those with non-polar solvents and a wide range of other cellular components may be extracted in addition to the oils, for example phospholipids and cell wall components. Evaporation of the water-miscible solvent leaves a residue which must therefore be purified further.

By "oils" is meant materials which are liquid at the extraction temperature and which are sparingly soluble in water.

In general oils recovered from microorganisms are triglycerides.

This invention comprises a process in which an oil is extracted from oil containing microorganisms which comprises disintegrating the microorganisms and contacting them in the presence of a water content of at least 70% by weight of that originally present in the cellular material and preferably in the presence of substantially all of the original water content of the microorganisms with a water immiscible solvent for the oil, separating the solvent from the microorganisms and recovering the oil from the solvent.

The invention also comprises a process for extracting a triglyceride from microbial matter containing it in which the triglyceride is released from the cells by pressure homogenisation and the released triglyceride is then extracted by contacting the microbial matter with a water-immiscible solvent for example an alkane suitably having 4 to 12 and preferably 5 to 8 carbon atoms, for example cyclohexane or preferably hexane. The invention avoids the requirement for dehydrating the microbial matter whilst permitting a good selectivity of extraction into the water-immiscible solvent to be secured.

It is preferred that the microorganism should be disintegrated in the presence of an aqueous culture medium in which it has been cultured, as this avoids the need for separating the microbial matter from the culture medium prior to the process. Typically the organism will constitute 5% to 20% by volume of the culture medium. The same solvent may be re-used two or more times for extracting successive quantities of disintegrated organism containing triglycerides, thus increasing the triglyceride content of the solvent. This leads to economies in recovering the triglyceride from the solvent by evaporation. Such processes may, if desired, be conducted by countercurrent extraction. Suitably, this may be carried out by using a solvent which is less dense than the phase containing the disintegrated microorganism and feeding it at a lower level than a phase which contains the disintegrated microorganism to a vessel in which extraction occurs. The vessel may be provided with baffles, restricting vertical flow, which define contact zones between the baffles and in which means is provided for stirring material in the contact zones.

If desired, separated solvent containing the triglyceride may be used together with fresh solvent to extract previously unextracted microorganisms. The solvent may be separated by centrifuging. The solvent may suitably be a hydrocarbon, for example an alkane which suitably has 4 to 12 and preferably 6 to 10 carbon atoms and is suitably hexane.

The organisms may be disintegrated by enzyme cell disruption using cell wall lytic enzymes, mechanical methods such as bead milling, colloid milling, disruption by pressure release, impinging jets, ultrasonication and preferably using high shear mixing and/or high pressure homogenisation. The disruption should be sufficient to disrupt the cell wall, thus enhancing the access of the solvent to the triglycerides contained within the cell. Any form of pressure homogeniser may be employed for this purpose.

In general in solvent extraction processes, small quantities of solvent are used compared with the material which is to be extracted. This has the advantage of achieving a high concentration of the desired solute in the solvent phase but when microbial materials are extracted in this way there is a tendency for organic matter present to act as an emulsifying agent, leading to the formation of a solvent-in-water emulsion of high stability. In order to reduce the stability of such emulsions, it may be necessary to add demulsifying agents thus enabling the emulsion to be separated suitably using high gravity conditions. However, the demulsifying agent may contaminate the product which it is desired to separate and involves additional cost. Contamination may be particularly undesirable if the demulsifier is toxic.

We have found that by operating in the presence of high concentrations of solvent sufficient to form a water-in-solvent dispersion, the dispersion is less stable and may be more readily separated in the absence of a demulsifying agent, for example by gravity settling or use of a centrifuge. It is desirable in this case to increase the triglyceride content of the solvent by extracting successive quantities of microbial material with it.

This invention therefore comprises a process as aforesaid in which the disintegrated microorganisms are contacted with a continuous phase of the solvent. It is desirable that the ratio of solvent phase to other matter present during the extraction step should be at least 1 to 1, preferably at least 1.5 to 1 and more preferably at least 2 to 1 and suitably at most 10 to 1 and preferably at most 1 to 1.

EXAMPLE 1

A strain of *Mortierella alpina* was grown in batch culture in an aqueous medium on a mixture of glucose and yeast autolysate to give a culture containing 54.8 g/l of cells containing 24% w/w of a triglyceride oil. The fatty acid composition of this oil was determined to be 18.6% w/w 5,8,11,14-eicosatetraenoic acid (arachidonic acid).

The cell suspension was dispersed using a high shear mixer (Ultra Turrax, IKA) then fed to a high pressure homogeniser (Rannie Lab homogeniser, APV) operating at a pressure of 400 bar. The resulting cell homogenate was then first mixed with a demulsifying agent (Armogard D5390, Akzo-Nobel, Littleborough) to give a concentration of the demulsifier of 2000 ppm. This aqueous phase was then contacted (at ambient temperature and neutral pH) with hexane by high shear mixing (Ultra Turrax, IKA) to ensure good phase contact. A phase ratio of 3:1 aqueous to solvent was used. The resulting emulsion was separated by centrifugation at 3000 g for 3 minutes. The separated hexane phase was purified from residual fermentation antifoam by passing through a silica gel column (Waters Sep-pak) and evaporated to give the purified triglyceride oil. This oil was analysed for 5,8,11,14-eicosatetraenoic acid content by Gas Chromatography. The overall triglyceride yield from hexane contact of the aqueous phase was 65.7% based on the initial oil content of the microbial cells. The 5,8,11,14-eicosatetraenoic acid content of the oil was 28.1% w/w.

In comparison a sample of fermenter culture was taken and the cells recovered by filtration. The collected cells were dried by freeze drying then mixed with hexane. 5 g of dried cells were contacted with 25 ml of hexane. The solvent was contacted with the cells for 60 minutes at ambient temperature before the solvent extract was recovered by filtration of the suspension. The solvent was purified of residual fermentation antifoam using a silica gel column (Waters Sep-pak) and evaporated to give a purified triglyceride oil. The overall triglyceride yield was 59% based on the initial oil content of the microbial cells. This was analysed for 5,8,11,14-eicosatetraenoic acid by Gas Chromatography giving a concentration of 7.1% w/w.

This shows that considerable breakdown of the 5,8,11,14-eicosatetraenoic acid had occurred during the extraction of dried cells compared to the extraction from homogenised whole cell culture.

Oil yield was higher from extraction from high pressure homogenised whole cells compared to freeze dried cells and the oil quality was higher in terms of the recovered 5,8,11,14-eicosatetraenoic acid.

EXAMPLE 2

A strain of *Mortierella alpina* was grown in batch culture in an aqueous medium on a mixture of glucose and yeast autolysate to give a culture containing 46.0 g/l of cells containing 51.0% w/w of a triglyceride oil. The fatty acid composition of this oil was determined to be 25.1% w/w 5,8,11,14-eicosatetraenoic acid (arachidonic acid).

The cell suspension was dispersed using a high shear mixer (Ultra Turrax) then fed to a high pressure homogeniser (Rannie) operating at a pressure of 400 bar. This aqueous phase was then contacted (at ambient temperature and neutral pH) with different quantities of hexane by high shear mixing (Ultra Turrax) to ensure good phase contact. Phase ratios of 1:1, 1:1.5, 1:2, 1:2.5, and 1:3 aqueous to solvent were used. The resulting mixed phases were separated by centrifugation in graduated test tubes at 3000 g for 3 minutes and the recovery of the initial solvent phase measured.

TABLE 1

| Phase ratio (aqueous:solvent) | Solvent recovery (%) |
|---|---|
| 3:1 | 4 |
| 2:1 | 15 |
| 1:1 | 88 |
| 1:1.5 | 95 |
| 1:2 | 97 |
| 1:2.5 | 101 |
| 1:3 | 100 |

In the case of the sample prepared using a phase ratio of 1:2 aqueous:solvent the solvent phase was recovered and the aqueous phase recontracted with sufficient hexane solvent to give a phase ratio of 1:2 aqueous:solvent. As for the original extraction a high shear mixer was used to ensure good contact of the phases. The pooled hexane phases were evaporated and analysed for total triglyceride content and of 5,8,11,14-eicosatetraenoic acid. The total triglyceride yield was 76% and the 5,8,11,14-eicosatetraenoic acid content of the oil was 29.2% w/w.

EXAMPLE 3

A strain of Thraustochytrium was grown in batch culture in an aqueous medium on a mixture of glucose, yeast extract, peptone and 20 g/l $Na_2SO_4$ to give a culture containing 15 g/l of cells containing 30% w/w of a triglyceride oil. The composition of the fatty acids of this oil was determined to be 10% w/w 7,10,13,16,19-docosahexaenoic acid (DHA).

The cell suspension was passed twice through a high pressure homogenised (Niro-Soavi Panda Laboratory homogeniser) operating at a pressure of 500 bar.

This aqueous phase was then contacted (at ambient temperature and neutral pH) with three times the aqueous phase volume of hexane by high shear mixing (Ultra Turrax, IKA) to ensure good phase contact.

The resulting mixed phases separated under gravity and the solvent phase recovered and retained.

The aqueous phase was contacted again with hexane (volume equal to three times the aqueous phase volume) and the hexane extract separated by gravity settling.

The pooled hexane phases were evaporated and analysed for total triglyceride content and of 4,7,10,13,16,19- docosahexaenoic acid (DHA).

The total triglyceride yield was 91% and the 4,7,10,13,16,19- docosahexaenoic acid (DHA) content of the oil was 8.7% w/w. The peroxide value (PV) of the oil was measured to be less than 5 milliequivalents of active oxygen per kg.

What is claimed is:

1. A process for extracting a triglyceride oil from triglyceride oil containing microorganisms which have been grown in aqueous culture medium and which have cell walls and which contain water, said process comprising disintegrating the microorganisms by mechanical means or enzymatically in the presence of the aqueous culture medium, and without separating said microorganisms from the aqueous culture medium prior to the disintegrating step, then contacting the disintegrated microorganisms in the aqueous culture medium with a water-immiscible organic solvent for the triglyceride oil whereby the triglyceride oil is extracted into the solvent, separating the solvent containing the extracted triglyceride oil from the aqueous culture medium containing the microorganisms and recovering the triglyceride oil from the separated solvent.

2. The process as claimed in claim 1 in which the triglyceride oil is oxygen- or heat-sensitive.

3. The process as claimed in claim 1 in which the disintegrated organisms are repeatedly contacted with solvent thereby extracting successive quantities of oil therefrom.

4. The process as claimed in claim 1 in which disintegrated microorganisms are extracted with solvent which contains triglyceride oil from a previous extraction of disintegrated microorganisms.

5. A process as claimed in claim 4 which is carried out by counter-current extraction.

6. The process as claimed in claim 5 in which the solvent is less dense than the phase containing the disintegrated microorganisms and is fed to a vessel in which extraction occurs at a lower level than the phase containing the disintegrated microorganisms.

7. The process as claimed in claim 5 in which the solvent is more dense than the phase containing the disintegrated microorganisms and is fed to a vessel in which extraction occurs at a higher level than the phase containing the disintegrated microorganisms.

8. The process as claimed in claims 6 or 7 in which the vessel is provided with baffles restricting vertical flow which define contact zones between the baffles and means for stirring material in the contact zones.

9. The process as claimed in claim 1 which comprises separating the solvent by centrifuging.

10. The process as claimed in claim 1 in which the disintegrated microorganisms are contacted with a continuous phase of the solvent.

11. The process as claimed in claim 9 in which during extraction the ratio of solvent phase to other matter present is at least 1 to 1.

12. The process as claimed in claim 1 in which the cells are disintegrated by pressure homogenization.

13. The process as claimed in claim 1 in which the solvent is a hydrocarbon.

14. A process as claimed in claim 13 in which the hydrocarbon is hexane.

15. A process as claimed in claim 1 in which the microorganism is *Mortierella alpina*.

16. The process as claimed in claim 11 wherein the ratio of solvent phase to other matter present is at least 2:1 and at most 10:1.

17. The process as claimed in claim 16 wherein the ratio is 5:1.

18. The process as claimed in claim 1 in which the microorganism is Thraustrochytrium.

* * * * *